(12) United States Patent  
Henry (10) Patent No.: US 11,998,872 B2
(45) Date of Patent: Jun. 4, 2024

(54) BIOGAS UPGRADING APPARATUS AND PROCESS

(71) Applicant: Air Products and Chemicals, Inc., Allentown, PA (US)

(72) Inventor: Donald E. Henry, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 243 days.

(21) Appl. No.: 17/498,890

(22) Filed: Oct. 12, 2021

(65) Prior Publication Data

US 2023/0114525 A1   Apr. 13, 2023

(51) Int. Cl.
*B01D 53/22* (2006.01)
*C10L 3/10* (2006.01)
*C12M 1/00* (2006.01)

(52) U.S. Cl.
CPC ......... *B01D 53/226* (2013.01); *B01D 53/227* (2013.01); *C10L 3/104* (2013.01); *C12M 47/18* (2013.01); *B01D 2256/245* (2013.01); *B01D 2257/504* (2013.01); *B01D 2258/05* (2013.01)

(58) Field of Classification Search
None
See application file for complete search history.

(56) References Cited

U.S. PATENT DOCUMENTS

| 8,999,038 | B2 | 4/2015 | Ungerank et al. |
| 9,050,553 | B2 | 6/2015 | Alizadeh-Khiavi et al. |

| 2009/0178557 | A1* | 7/2009 | Kulkarni | B01D 53/228 95/45 |
| 2011/0094378 | A1 | 4/2011 | Mitariten | |
| 2012/0123079 | A1* | 5/2012 | Ungerank | B01D 53/228 528/80 |

(Continued)

FOREIGN PATENT DOCUMENTS

| EP | 1634946 | 7/2011 |
| WO | 2020069868 | 4/2020 |

OTHER PUBLICATIONS

Xiao Yuan Chen, et al, "Membrane gas separation technologies for biogas upgrading", RSC Advances, vol. 5, No. 31, Jan. 1, 2015, pp. 24399-24448.

(Continued)

*Primary Examiner* — Jason M Greene
(74) *Attorney, Agent, or Firm* — Amy Carr-Trexler (57) ABSTRACT

A biogas upgrading system can include a multiple stage membrane system that is configured to remove oxygen so that the biogas is upgraded to have a higher concentration of methane, a pre-selected oxygen ($O_2$) concentration (e.g. less than or equal to 0.2 mol %, etc.), and a pre-selected carbon dioxide ($CO_2$) concentration (e.g. less than or equal to 5 mol %, etc.). The membrane system can be configured to reject $O_2$ by utilizing a low $CO_2/O_2$ selectivity that is within a pre-determined range (e.g. less than 5 or less than 4.5). In some embodiments, the upgraded biogas that is output from the system can be entirely made up of methane, carbon dioxide, and oxygen. In other embodiments, the biogas can be almost entirely composed of these components along with a small amount of nitrogen and a trace amount (e.g. less than or equal to 0.2%-0.1%, etc.) of other components.

20 Claims, 3 Drawing Sheets

(56) References Cited

U.S. PATENT DOCUMENTS

2015/0336046 A1* 11/2015 Ungerank ............ B01D 53/226
                                                      96/7
2017/0304769 A1* 10/2017 Bigeard ............... B01D 53/226
2018/0112142 A1   4/2018 Foody et al.
2019/0030482 A1   1/2019 Ding et al.
2019/0224617 A1*  7/2019 Mitariten ............. B01D 53/226

OTHER PUBLICATIONS

Chen Zhaoyu, et al, "A simple self-regulating permeability and selectivity of poly (arylene ether ketone) with amino groups for gas separation membrane", Journal of Polymer Research, Springer Netherlands, Dordrecht, vol. 26, No. 12, Nov. 14, 2019, pp. 1-8.

* cited by examiner

BIOGAS UPGRADING APPARATUS AND PROCESS

FIELD

The present innovation relates to biogas upgrading systems, membrane arrangements, and apparatuses utilizable in such systems, and methods of making and using the same.

BACKGROUND

Raw biogas can be upgraded to higher purity methane streams for downstream use (e.g. injection into a pipeline, use in a combined heat and power plant (CHP), etc.). Biogas is often purified so that the major component of the biogas is methane.

Biogas is often defined as the product of an anaerobic digestion of organic waste. The biogas that is produced from the anaerobic digestion of organic waste can often contain methane, carbon dioxide, nitrogen, oxygen, hydrogen sulfide, and siloxanes. Capturing and upgrading biogas can help reduce greenhouse gas emissions and create renewable energy that can be sold.

Examples of systems that can be used to process raw biogas to obtain high purity methane can be appreciated from U.S. Pat. Nos. 9,050,553 and 8,999,038, U.S. Pat. App. Pub. No. 2011/0094378, International Publication No. WO 2006/069868, and EP 1 634 946.

Conventional purification methods used to help upgrade the biogas include water washing, amine scrubbing, catalytic systems, or pressure swing adsorption (PSA) to remove carbon dioxide and other contaminants. The PSA process can be costly to build and operate. Catalytic systems are often costly to operate as well because they utilize consumable elements (e.g. catalyst material that can be poisoned) and produce unwanted byproducts (e.g. water) that must be removed downstream.

SUMMARY

A new system is needed to upgrade biogas so it can be more easily utilized in downstream operations (e.g. providing to a pipeline, use in a CHP system, etc.). In some embodiments, the biogas can be referred to as a biomethane gas, a landfill gas, or a biofuel. In some embodiments, a multistage membrane system can be utilized to process a biogas from a biogas system to increase the methane concentration while also removing oxygen and carbon dioxide from the biogas so that the oxygen and carbon dioxide within the upgraded biogas output from the membrane system are within pre-selected oxygen and carbon dioxide concentrations in which the oxygen concentration is less than or equal to 0.2% of the upgraded biogas output stream. The pre-selected carbon dioxide concentration in the upgraded biogas output stream in such embodiments can be less than 2%. Preferably, embodiments of the system can be configured to avoid use of PSA and also avoid use of a catalytic system to remove oxygen from the upgraded biogas. Oxygen can also be referred to herein as $O_2$, carbon dioxide can also be referred to herein as $CO_2$, and methane can also be referred to herein as $CH_4$.

For example, in some embodiments, a biogas upgrading system can include a multiple stage membrane system that is configured to remove oxygen so that the biogas is upgraded to have a higher concentration of methane that is at a pre-selected methane concentration (e.g. 94%, greater than or equal to 94%, 96%, greater than or equal to 96%, greater than 97%, greater than or equal to 97%, greater than or equal to 99.5%, etc.), a pre-selected oxygen concentration (e.g. less than 1%, less than 0.2%, or less than or equal to 0.2%), and a pre-selected carbon dioxide concentration (e.g. less than or equal to 5%, less than or equal to 2%, less than or equal to 0.5%, etc.). The concentration percentages discussed herein can be a volume fraction (vol %) or a molar fraction (mol %).

In some embodiments, the membrane system can include multiple stages that each include at least one membrane that can be configured to reject $O_2$ by utilizing a low $CO_2/O_2$ selectivity that is within a pre-determined range (e.g. less than 5.0 or less than 4.5, etc.) to form the upgraded methane output flow. In some embodiments, the upgraded biogas that is output from the system can be entirely made up of methane, $CO_2$, and $O_2$. In other embodiments, the biogas can be almost entirely composed of these components along with a small amount (e.g. less than 5%-1%) of nitrogen and/or a trace amount (e.g. less than 0.2%-0.1%, etc.) of other components (e.g. hydrogen sulfide, etc.).

For example, some embodiments of a biogas upgrading system can include a multiple stage membrane system that is configured to remove oxygen and carbon dioxide so that the biogas is upgraded to have a higher concentration of methane (e.g. at least 95% methane, at least 97% methane, at least 99.5% methane, etc.) and a level of oxygen that is at or below a pre-selected oxygen concentration (e.g. less than 3%, less than 1%, up to 0.2% or less than 0.2%) while maintaining a high level of methane recovery (e.g. over 90% methane recovery, over 95% methane recovery, between 95-98% methane recovery, between 98% to 99.5% methane recovery, etc.), where recovery is defined as the ratio of methane in the product flow to methane in the feed flow. The biogas that is output from the upgrading system can also include carbon dioxide within a pre-selected compositional range (e.g. up to 5%, less than 2%, less than or equal to 2%, 0.5%, less than or equal to 0.5%, etc.). The one or more membranes used in each stage of the membrane system can be configured to have a $CO_2/O_2$ selectivity of less than 5 or less than 4.5.

In some embodiments, the membrane system can be configured so that the oxygen rejection factor (e.g. the molar concentration of $O_2$ within the feed as compared to the molar concentration of $O_2$ within the upgraded biogas output from the membrane system, mol % $O_2$ feed/mol % $O_2$ output, is within a pre-determined range (e.g. more than 5, more than 1.0, more than 0.75, between 1.0 and 1.25, between 0.75 and 1.25, within the range of 0.77-1.22, between 0.8 and 1.2, within the range of 0.7-1.3, within the range of 0.9-1.5 or within the range of 0.9-2.2, etc.).

In a first aspect, a process for purifying a biogas feed flow via removal of oxygen ($O_2$) and carbon dioxide ($CO_2$) can include providing the biogas feed flow to a first stage of a membrane system to produce a first stage nonpermeate flow and a first stage permeate flow. The first stage nonpermeate flow can be comprised of methane, $O_2$, and $CO_2$ such that the first stage nonpermeate flow has a lower concentration of $CO_2$ than the first stage permeate flow. The first stage permeate flow can be comprised of methane, $O_2$, and $CO_2$ and can have a lower methane concentration than the first stage nonpermeate flow. The process can also include supplying the first stage nonpermeate flow to a second stage of the membrane system to produce a second stage nonpermeate flow and a second stage permeate flow. The second stage nonpermeate flow can comprise at least 90 mol % methane and less than 1 mol % $O_2$. The second stage permeate flow can have a $CO_2$ content that is greater than a $CO_2$ content of the second stage nonpermeate flow.

Embodiments of the process can also include supplying the first stage permeate flow to a third stage of the membrane system to produce a third stage nonpermeate flow and a third stage permeate flow and providing the third stage nonpermeate flow to form a recycling stream for feeding the third stage nonpermeate flow to the first stage or a compressor system. For example, the recycling that is performed can include mixing the third stage nonpermeate flow with the second stage permeate flow to form the recycling stream before feeding the recycling stream to the compressor system for undergoing compression to a pre-selected pressure. In some aspects, the process can also include mixing the recycling stream with the biogas feed flow before the biogas feed flow is fed to the compressor system, the compressor system being upstream of the membrane system.

An aspect of the process for purifying a biogas feed flow can also include supplying the first stage permeate flow to a third stage of the membrane system to produce a third stage nonpermeate flow and a third stage permeate flow. At least one membrane of the first stage can have a $CO_2/O_2$ selectivity value of less than 5.0, less than 4.5, less than 4.0, less than or equal to 3.5, between 3.0 and 5.0, or between 3.4 and 4.5 and at least one membrane of the third stage can have a $CO_2/O_2$ selectivity value of less than 5.0, less than 4.5, less than 4.0, less than or equal to 3.5, between 3.0 and 5.0, or between 3.4 and 4.5. In some embodiments, at least one membrane of the first stage can have a $CO_2/O_2$ selectivity value of less than 5.0, less than 4.5, less than 4.0, less than or equal to 3.5, between 3.0 and 5.0, or between 3.4 and 4.5. In some aspects of the process, each and every membrane of the first stage, each and every membrane of the second stage, and/or each and every membrane of the third stage has a $CO_2/O_2$ selectivity value of less than 5, less than 4.5, between 3.0 and 5.0, or between 3.4 and 4.5.

Embodiments of the process can be performed so that an oxygen reduction factor is greater than 1.0 or between 1.0 and 1.25. The oxygen reduction factor can be a ratio of a molar concentration of $O_2$ within the biogas feed flow and a molar concentration of $O_2$ within the second stage nonpermeate flow.

Embodiments of the process can be implemented so that the second stage nonpermeate flow is an upgraded biogas output flow having a methane content of at least 95 mol % methane (e.g. 95 mol %-100 mol %), at least 98 mol % methane (e.g. 98 mol %-100 mol %), or at least 99.5 mol % methane (e.g. (e.g. 99.5 mol %-100 mol %).

In some embodiments of the process, the second stage nonpermeate flow has less than 0.2 mol % $O_2$. In other embodiments of the process, the second stage nonpermeate flow has less than or equal to 0.2 mol % $O_2$ and has greater than or equal to 0.05 mol % $O_2$. In other embodiments of the process, the second stage nonpermeate flow has less than or equal to 0.2 mol % $O_2$ and has greater than or equal to 0.1 mol % $O_2$. In such embodiments, the $CO_2$ concentration of the second stage nonpermeate flow can be less than or equal to 2 mol % $CO_2$, less than or equal to 5 mol % $CO_2$, or be within a different pre-selected $CO_2$ concentration range.

Embodiments of a biogas upgrading system are also provided. Embodiments can be arranged and configured to implement embodiments of the process for purifying a biogas feed flow. Embodiments of the biogas upgrading system can include a membrane system configured to receive a biogas feed flow output from a biogas system. The membrane system can include a first stage positioned and configured to receive the biogas feed flow to produce a first stage nonpermeate flow and a first stage permeate flow. The first stage nonpermeate flow can be comprised of methane, $O_2$, and $CO_2$ such that the first stage nonpermeate flow has a lower concentration of $CO_2$ than the first stage permeate flow. The first stage permeate flow can be comprised of methane, $O_2$, and $CO_2$ and have a lower methane concentration than the first stage nonpermeate flow. A second stage can be connected to the first stage to receive the first stage nonpermeate flow to produce a second stage nonpermeate flow and a second stage permeate flow. The second stage nonpermeate flow can include at least 90 mol % methane and less than 1 mol % $O_2$. The second stage permeate flow can have a $CO_2$ content that is greater than a $CO_2$ content of the second stage nonpermeate flow.

Embodiments of the biogas upgrading system can be configured so that the membrane system also includes a third stage connected to the first stage to receive the first stage permeate flow and produce a third stage nonpermeate flow and a third stage permeate flow. The third stage can be connected to a recycle conduit such that the third stage nonpermeate flow is passable through the recycle conduit to a position upstream of the first stage of the membrane system.

For example, some embodiments of the biogas upgrading system can include a compressor system positioned upstream of the first stage to compress the biogas feed flow before the biogas feed flow is fed to the first stage. The third stage can be connected to the recycle conduit such that the third stage nonpermeate flow is passable through the recycle conduit to the compressor system without use of another compressor system. The recycle conduit is configured to mix the third stage nonpermeate flow with the second stage permeate flow to form a recycling stream before feeding the recycling stream to the compressor system for undergoing compression to a pre-selected pressure.

For embodiments of the biogas upgrading system, the second stage nonpermeate flow can have less than 0.2 mol % $O_2$, or can have less than or equal to 0.2 mol % $O_2$ and have greater than or equal to 0.05 mol % $O_2$. In other embodiments of the system, the second stage nonpermeate flow can have less than or equal to 0.2 mol % $O_2$ and have greater than or equal to 0.1 mol % $O_2$ or have another pre-selected oxygen content that is within a different range involving oxygen concentrations of less than 1 mol % $O_2$ or less than or equal to 0.2 mol % $O_2$. In such embodiments, the $CO_2$ concentration of the second stage nonpermeate flow can be less than or equal to 2 mol % $CO_2$, less than or equal to 5 mol % $CO_2$, or be within a different pre-selected $CO_2$ concentration range.

In some embodiments, at least one membrane of the first stage, at least one membrane of the second stage, and/or at least one membrane of the third stage has a $CO_2/O_2$ selectivity value of less than 5.0, less than 4.5, less than 4.0, less than or equal to 3.5, between 3.0 and 5.0, or between 3.4 and 4.5. For example, embodiments of the biogas upgrading system can be configured so that at least one membrane of the first stage has a $CO_2/O_2$ selectivity value of less than 5.0, less than 4.5, less than 4.0, less than or equal to 3.5, between 3.0 and 5.0, or between 3.4 and 4.5. As another example, each and every membrane of the first stage, each and every membrane of the second stage, and/or each and every membrane of the third stage can have a $CO_2/O_2$ selectivity value of less than 5.0, less than 4.5, less than 4.0, less than or equal to 3.5, between 3.0 and 5.0, or between 3.4 and 4.5.

Embodiments of the biogas upgrading system can be configured so that an oxygen reduction factor is greater than 1.0 or between 1.0 and 1.25. The oxygen reduction factor can be a ratio of a molar concentration of $O_2$ within the biogas feed flow and a molar concentration of $O_2$ within the second stage nonpermeate flow.

Embodiments of the biogas upgrading system can be configured so that the second stage nonpermeate flow is an upgraded biogas output flow having a methane content of at least 95 mol % methane (e.g. 95 mol %-100 mol %), at least 98 mol % methane (e.g. 98 mol %-100 mol %), or at least 99.5 mol % methane (e.g. (e.g. 99.5 mol %-100 mol %). Some embodiments can be designed to provide a recovery of greater than 95% methane, greater than 98 methane, or greater than 99% methane.

Embodiments of the biogas upgrading system can include the biogas system. The biogas system can include at least one digester (e.g. an anaerobic digester) that forms the biogas feed flow and at least one biogas cleaning device positioned to treat the biogas feed flow before the biogas feed flow is fed to the first stage of the membrane system. The biogas system can be positioned to feed the biogas feed flow to a compressor system for feeding a compressed biogas feed flow to the first stage of the membrane system. The membrane system can include a second stage and a third stage as discussed herein as well.

Other details, objects, and advantages of the biogas upgrading systems, membrane arrangements and apparatuses utilizable in such systems, and methods of making and using the same will become apparent as the following description of certain exemplary embodiments thereof proceeds

BRIEF DESCRIPTION OF THE DRAWINGS

Exemplary embodiments of biogas upgrading systems, membrane arrangements and apparatuses utilizable in such systems, and methods of making and using the same are shown in the drawings included herewith. It should be understood that like reference characters used in the drawings may identify like components.

DETAILED DESCRIPTION OF EXEMPLARY EMBODIMENTS

Figure 1:
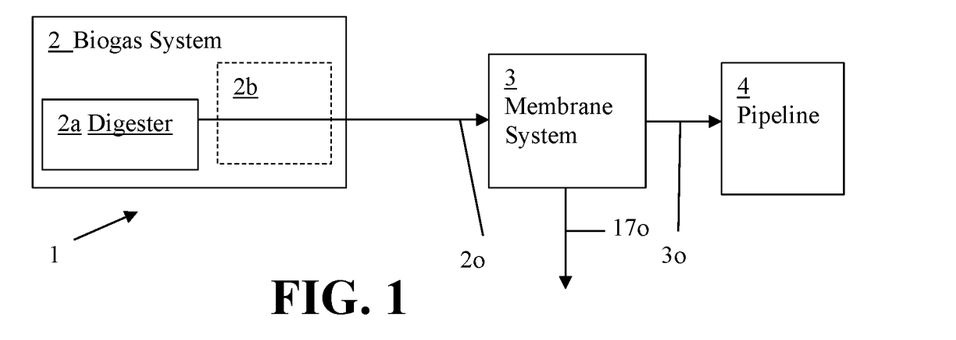
FIG. 1 is a box diagram of a first exemplary embodiment of a biogas upgrading system.
Figure 2:
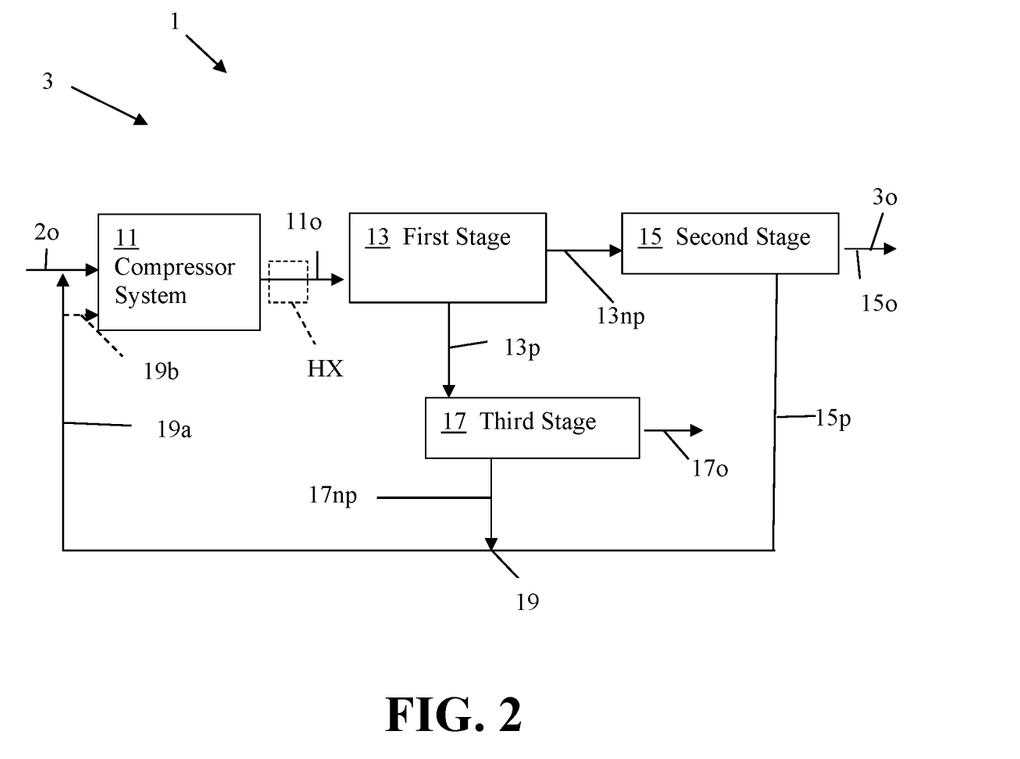
FIG. 2 is a schematic view of a first exemplary embodiment of an exemplary multiple stage membrane system that can be used in the first exemplary embodiment of the biogas upgrading system. It should be appreciated that the compressor system 11 and the compressed feed cooler HX shown in broken line can be included in embodiments of the membrane system 3, or can be separate components that are between the biogas system 2 and the membrane system 3, or are part of the biogas system 2 that are arranged to compress the biogas feed flow 2o and subsequently cool that compressed feed flow before the feed flow is fed to the membrane system 3.

Referring to FIGS. 1-2, a biogas upgrading system 1 can be configured to receive a biogas feed flow 2o from a biogas system 2. The biogas system can include a digester 2a that treats farm waste, energy crops, or other biogas production materials (e.g. biodegradable waste, sewage sludge, food waste, etc.) to form the biogas feed flow 2o. The digester 2a can be an anaerobic digester, for example.

The biogas feed flow 2o can include methane as well as other components, such as, for example, nitrogen, carbon dioxide, oxygen, siloxanes, and hydrogen sulfide. The biogas feed flow 2o can be fed to a membrane system 3 to improve the purity of methane within the biogas so that an upgraded biogas output flow 3o is feedable to a pipeline 4 or other downstream device (e.g. a CHP, etc.). At least one feed conduit can be positioned to guide the biogas feed flow 2o from the biogas system 2 to the membrane system 3. The membrane system 3 can be a multiple stage membrane system 3.

In some embodiments, the biogas system 2 can be configured to clean the biogas output from the digester 2a to form the biogas feed flow 2o before it is fed to a membrane system 3 so that the biogas feed flow 2o fed to the membrane system consists of methane, oxygen, and carbon dioxide or consists essentially of methane, oxygen, and carbon dioxide while also containing a small amount of nitrogen (e.g. up to 5% nitrogen, up to 2% nitrogen, etc.) and trace amounts of other components (e.g. one or more of water, hydrogen sulfide, siloxanes, etc.). The trace amounts of the other components in such embodiments can be less than 0.5%, less than 0.2%, or less than 0.1% of the overall composition of the biogas feed flow in some embodiments that have such trace components.

For example, biogas output from the digester 2a can be fed to at least one biogas cleaning device 2b so that the biogas is cleaned to remove all, or substantially all of the siloxanes, hydrogen sulfide and/or other components to form the biogas feed flow 2o. The at least one biogas cleaning device 2b can include an arrangement of one or more biogas cleaning devices 2b (e.g. coalescing filters, one or more adsorption systems, or other biogas conditioning devices, etc.) positioned between the membrane system 3 and the digester 2a to clean the biogas before the biogas feed flow 2o is fed to the membrane system 3 configured to improve the methane concentration of the biogas to a pre-selected higher concentration.

Biogas cleaning conduit(s) can be positioned to feed the biogas from the digester 2a to the at least one biogas cleaning device 2b and between different biogas cleaning devices 2b. There can be a biogas feed conduit positioned between the most downstream biogas cleaning device and a compressor system 11. A biogas membrane system feed conduit can be positioned to feed the compressed biogas feed flow 11o output from the compression system 11 to the first stage 13 of the membrane system 3.

The biogas feed flow 2o output from the biogas system 2 can include methane at a first raw biogas feed methane concentration, carbon dioxide at a first raw biogas carbon dioxide feed concentration, and oxygen at a first raw biogas feed oxygen concentration. In some embodiments, the first raw biogas feed methane concentration can be in the range of 30%-80% methane (e.g. 40%, 50%, 60%, 70%, or 75% methane, etc.), the first raw biogas carbon dioxide feed concentration can be in a range of 20%-70% (e.g. 25%, 30%, 40%, 50%, 60%, 70%, etc.), and the first raw biogas feed oxygen concentration can be in a range less than 0.2% to less than or equal to 2% (e.g. less than 0.3%, less than 0.4%, less than 1%, less than 1.5%, up to 2%, etc.). As noted above, it should be understood that the concentration percentages discussed herein can be a volume fraction (vol %) or a molar fraction (mol %).

As discussed above, the biogas feed flow 2$o$ output from the biogas system 2 can be fed to the membrane system 3. The membrane system 3 can be a membrane arrangement structured as a multiple stage membrane system that is configured to remove oxygen and carbon dioxide so that the biogas is upgraded to form an upgraded biogas output flow 3$o$ that has a higher concentration of methane ($CH_4$) and a level of oxygen ($O_2$) that is at or below a pre-selected $O_2$ concentration and a carbon dioxide ($CO_2$) concentration that is at or below a pre-selected $CO_2$ concentration. For example, the upgraded biogas that is output can include $CO_2$ within a pre-selected compositional range (e.g. up to 5%, less than 2%, less than or equal to 2%, less than 1%, less than 0.5%, less than or equal to 0.5%, less than 0.1%, etc.) and $O_2$ within a pre-selected compositional range (e.g. up to 1%, less than 1%, up to 0.3%, less than 0.3%, up to 0.2%, or less than 0.2%, etc.). In some embodiments, the upgraded biogas output flow 3$o$ can consist of or consist essentially of $CH_4$ within a pre-selected compositional range of $CH_4$ (e.g. greater than or equal to 94% $CH_4$, greater than or equal to 95% $CH_4$, greater than or equal to 98% $CH_4$, greater than or equal to 99.5% $CH_4$, etc.), $CO_2$ within a pre-selected compositional range (e.g. up to 5%, less than 2%, less than or equal to 2%, 0.5%, less than or equal to 0.5%, etc.) and $O_2$ within a pre-selected compositional range (e.g. 0.2% or less than 0.2% or less than or equal to 0.2%, etc.). As noted above, it should be understood that the concentration percentages discussed herein can be a volume fraction (vol %) or a molar fraction (mol %).

There can be at least one membrane used in each stage of the membrane system 3 operating with a $CO_2/O_2$ selectivity that is within a pre-determined range (e.g. less than 5, less than 4.5, between 5.0 and 3.0, between 4.5 and 3.4, etc.). For example each stage of the membrane system 3 can include a single membrane or can utilize a plurality of membranes that are arranged in series or are arranged in parallel. The membrane system 3 can be configured so that the oxygen rejection factor (e.g. the concentration of $O_2$ within the biogas feed 2$o$ as compared to the concentration of $O_2$ within the upgraded biogas output 3$o$ from the membrane system, % $O_2$ feed/% $O_2$ output), is within a pre-determined range (e.g. more than 5, more than 1.0, more than 0.75, between 0.75 and 1.25, within the range of 0.77-1.22, between 0.8 and 1.2, within the range of 0.7-1.3, within the range of 0.9-1.5 or within the range of 0.9-2.2, etc.)

An example of the membrane system 3 can be appreciated from FIG. 2. It should be appreciated that the compressor system 11 and the compressed feed cooler HX shown in broken line in FIG. 2 can be included in embodiments of the membrane system 3, can be separate components that are between the biogas system 2 and the membrane system 3, or are part of the biogas system 2. There can also be other components upstream of the membrane system 3. For instance, a liquid removal device and a reheater can be positioned between the feed cooler HX and the membrane system 3 to remove liquid from the cooled feed and subsequently reheat the dried feed before it is fed to the membrane system 3. These components can be part of the biogas system 2 or part of the membrane system 3.

When the compressor system 11 and the compressed feed cooler HX are included in the biogas system 2, are arranged between the biogas system 2 and the membrane system 3, or are included in the membrane system 3, these components can be arranged so that the compressor system 11 compresses the biogas feed flow 2$o$ and subsequently cools that compressed feed flow before the feed flow is fed to the membrane system 3. Conduits can be positioned between the compressor system 11 and the compressed feed cooler HX and the compressed feed cooler HX and the first stage 13 of the membrane system 3 to guide the compressed biogas from the compressor system 11 to the first stage 13 of the membrane system 3 after being cooled to a desired pre-selected temperature within a pre-selected temperature range.

For example, the compressor system 11 can be positioned to receive the biogas feed flow 20 from the at least one biogas cleaning device 2$b$ to compress the biogas feed flow 2$o$ to a pre-selected pressure that is within a pre-selected pressure range to output a compressed biogas feed flow 11$o$. The pre-selected pressure can be, for example 14 barg (bar gauge pressure), 10 barg, 15 barg, or a pressure within the range of 10-15 barg, 10-16 barg, 5-15 barg, 5-20 barg, 5-25 barg, and the pre-selected pressure range can be a pressure range of 10-15 bar, 5-15 bar, or 5-20 bar or other pre-selected pressure range. In some embodiments, the compression system 11 can be configured as a single stage compressor, a multiple stage compressor or a series of compressors.

The compressed biogas feed flow 11$o$ can then be passed through at least one compressed feed cooler HX for cooling to a pre-selected temperature within a pre-selected temperature range. The pre-selected temperature can be, for example 20° C., 25° C., 30° C. or be a temperature within the range of 15° C.-25° C., 10° C.-30° C., or 0° C.-65° C., and the pre-selected temperature range can be a temperature range of 15° C.-25° C., 10° C.-30° C., 5° C.-40° C., 0° C.-50° C., 0° C.-65° C., or other pre-selected temperature range. In other embodiments, a feed cooler HX may not be utilized (e.g. embodiments where the compressed biogas feed flow 2$o$ can be within a desired pre-selected temperature range without need or after cooling). In such embodiments, the compressed biogas feed flow 11$o$ can be fed directly to the first stage 13 of the membrane system 3 via a compressed biogas feed conduit.

The first stage 13 of the membrane system 3 can include at least one membrane vessel retaining one or more membranes therein for fluid separation that includes a single membrane vessel or multiple membrane vessels that are arranged in parallel or in series. The first stage 13 can be fluidly connected to a second stage 15 and a third stage 17 of the membrane system 3. Stage conduits can be positioned to connect the first stage 13 to the second stage 15 and third stage 17 to guide fluid between these stages.

The second stage 15 can include at least one membrane vessel retaining one or more membranes therein for fluid separation that includes a single membrane vessel or multiple membrane vessels that are arranged in parallel or in series. Stage conduits can be positioned to connect the second stage 15 to the first stage 13 and the third stage 17 to guide fluid between these stages.

The third stage 17 can include at least one membrane vessel retaining one or more membranes therein for fluid separation that includes a single membrane vessel or multiple membrane vessels that are arranged in parallel or in series. A recycle stage conduit can be positioned to connect the third stage 17 to the compressor system 11 (e.g. upstream of the compressor system 11 for feeding to the compressor system 11, to a particular compressor stage of the compressor system, etc.). An output conduit can also be connected to the third stage 17 to guide fluid that is to be output from the third stage as exhaust or to transport that fluid to another unit within a plant for use therein (e.g. as a cooling or heating medium for a heat exchanger, etc.).

The first stage 13 can include at least one membrane that is designed so that the compressed biogas feed is passed into the first stage 13 and contacts the membrane structure within the vessel of the first stage. The first stage 13 of the membrane system 3 can include a single membrane or can utilize a plurality of membranes that are arranged in series or are arranged in parallel. Each membrane can be composed so that the $CO_2$ component of the biogas feed passes quickly through the membrane structure to be output as a first stage permeate gas flow 13p, or first stage fast gas flow, while the methane component of the biogas feed passes through the membrane structure at a substantially slower speed so that a substantial portion of the $CO_2$ can be separated from the methane within the biogas fed to the first stage 13 and the majority of the methane within the biogas flow fed to the first stage 13 can be output as a first stage nonpermeate flow 13np. The membrane(s) of the first stage 13 can be positioned and composed so that the $O_2$ within the biogas fed to the first stage 13 is substantially passed through the membrane structure under the operating conditions of the first stage 13 as well (e.g. is within the first stage permeate gas flow 13p that also includes a substantial part of the $CO_2$ of the biogas).

For example, the first stage permeate gas flow 13p output from the first stage 13 can be comprised mostly of $CO_2$ and can also include some methane and some $O_2$ therein. For example, the first stage permeate gas flow 13p can include $CO_2$ at a first stage $CO_2$ permeate gas flow concentration within a range of 60%-99% $CO_2$, 60%-95% $CO_2$, 60%-80% $CO_2$, 80%-90% $CO_2$, 70%-99% $CO_2$, 70%-97% $CO_2$, 75%-95% $CO_2$, 80%-95% $CO_2$, or 85%-95% $CO_2$. The first stage permeate gas flow 13p can include a first stage $O_2$ permeate gas flow concentration within a range of 0.2%-6% $O_2$, 0.1%-5% $O_2$, 0.2%-4% $O_2$, 0.2%-2% $O_2$, 0.2%-0.4% $O_2$, or 0.3%-0.35% $O_2$. The first stage permeate gas flow 13p can also include a first stage methane permeate gas flow concentration as the remaining portion of the permeate gas flow. For instance, first stage permeate gas flow 13p can also include a first stage methane permeate gas flow concentration that is within the range of 1%-40% $CH_4$, 3%-30% $CH_4$, 5%-25% $CH_4$, 5%-20% $CH_4$, 5%-40% $CH_4$, 10%-20% $CH_4$, 5%-15% $CH_4$, or 5%-30% $CH_4$. As mentioned previously, it should be appreciated that these exemplary concentration percentages discussed herein can be a volume fraction (vol %) or a molar fraction (mol %). The first stage permeate pressure can be maintained at a feed to permeate pressure ratio within the range of 1.5 to 15, 1.5 to 10, 2 to 10, or 3 to 7. The feed to permeate pressure ratio can be a ratio of feed pressure ($P_f$)/permeate pressure ($P_p$), $P_f/P_p$, where $P_f$ and $P_p$ are the feed and permeate pressures on either side of the membrane in absolute pressure rather than gauge pressure (e.g. ratio of $P_f/P_p$ for the first stage 13 can be [the pressure of the compressed biogas feed flow 11o]/[pressure of the first stage permeate gas flow 13p]).

The first stage nonpermeate gas flow 13np can be comprised mostly of methane and can also include some $CO_2$ and some $O_2$ therein. For example, the first stage nonpermeate gas flow 13np can include methane at a first stage methane nonpermeate gas flow concentration in a range of 50%-95% $CH_4$, 80%-90% $CH_4$, 60%-80% $CH_4$, 60%-90% $CH_4$, 65%-90% $CH_4$, 70%-85% $CH_4$, 75%-85% $CH_4$, or 70%-95% $CH_4$. The first stage nonpermeate gas flow 13np can include a first stage $O_2$ nonpermeate gas flow concentration within a range of 0.2%-5% $O_2$, 0.1%-5% $O_2$, 0.1%-4% $O_2$, 0.2%-4% $O_2$, 0.2%-2% $O_2$, 0.1%-0.4% $O_2$, 0.2%-0.5% $O_2$, 0.3%-0.35% $O_2$, or 0.2%-0.4% $O_2$. The first stage nonpermeate gas flow 13np can also include a first stage $CO_2$ nonpermeate gas flow concentration as the remaining portion of the nonpermeate gas flow. For instance, first stage nonpermeate gas flow 13np can also include a first stage $CO_2$ nonpermeate gas flow concentration that is within the range of 5%-50% $CO_2$, 5%-40% $CO_2$, 10%-40% $CO_2$, 10%-35% $CO_2$, 15%-20% $CO_2$, 0%-25% $CO_2$, 10%-30% $CO_2$, 10%-20% $CO_2$, or 15%-30% $CO_2$. As mentioned previously, it should be appreciated that these exemplary concentration percentages discussed herein can be a volume fraction (vol %) or a molar fraction (mol %). The pressure of the first stage nonpermeate gas flow 13np stream output from the first stage 13 can be nearly the same as the feed pressure of the feed fed to the first stage 13 (e.g. pressure of the compressed biogas feed flow 11o).

The first stage nonpermeate flow 13np can be fed to the second stage 15 of the membrane system 3 via a first stage nonpermeate flow conduit positioned between the first and second stages. The second stage 15 can include at least one membrane (e.g. can include a single membrane or can utilize a plurality of membranes that are arranged in series or are arranged in parallel). The membrane(s) of the second stage 15 can be configured so that the first stage nonpermeate flow 13np is passed into the second stage 15 and contacts the membrane structure within the vessel of the second stage 15. The membrane can be composed so that the $CO_2$ component of the first stage nonpermeate flow 13p passes quickly through the membrane structure to be output as a second stage permeate gas flow 15p, or fast gas flow, while the methane component of the first stage nonpermeate flow 13np fed to the second stage 15 passes through the membrane structure at a substantially slower speed so that a substantial portion of the $CO_2$ can be separated from the methane within the gas fed to the second stage 15 and the majority of the methane within the first stage nonpermeate flow 13np fed to the second stage 15 can be output as a second stage nonpermeate flow 15o.

The one or more membranes of the second stage 15 can be composed so that the $O_2$ within the first stage nonpermeate flow 13np fed to the second stage 15 passes through the membrane structure as well (e.g. is within the "fast gas" flow, or the second stage permeate gas flow 15p that also includes a substantial part of the $CO_2$ within the first stage nonpermeate flow 13np). The second stage permeate pressure can be maintained at a feed to permeate pressure ratio within the range of 1.5 to 100, 1.5 to 50, to 30, or 5 to 20. As noted above, the feed to permeate pressure ratio can be a ratio of feed pressure ($P_f$)/permeate pressure ($P_p$), $P_f/P_p$, where $P_f$ and $P_p$ are the feed and permeate pressures on either side of the membrane in absolute pressure rather than gauge pressure (e.g. ratio of $P_f/P_p$ for the second stage 15 can be [pressure of the first stage nonpermeate flow 13np]/[pressure of the second stage permeate gas flow 15p]).

The second stage permeate gas flow 15p output from the second stage 15 can be comprised mostly of $CO_2$ and can also include some methane and $O_2$ therein. For example, the second stage permeate gas flow 15p can include $CO_2$ at a second stage $CO_2$ permeate gas flow concentration of between 30%-80% $CO_2$, 40%-70% $CO_2$, 45%-65% $CO_2$, 50%-85% $CO_2$, 55%-75% $CO_2$, or 60%-80% $CO_2$. The second stage permeate gas flow 15p can include a second stage $O_2$ permeate gas flow concentration within a range of up to 6% $O_2$, up to 5% $O_2$, 0.2-1.0% $O_2$, 0.2-5.0% $O_2$, 0.5-3.0% $O_2$, or 0.45%-0.85% $O_2$. The second stage permeate gas flow 15p can also include a second stage methane permeate gas flow concentration as the remaining portion of the permeate gas flow. For instance, second stage permeate gas flow 15p can also include a second stage methane permeate gas flow concentration that is within the range of 20%-70% $CH_4$, 30%-60% $CH_4$, 35%-55% $CH_4$, 15%-50% $CH_4$, 20%-40% $CH_4$, 25%-45% $CH_4$, or 15%-20% $CH_4$. As mentioned previously, it should be appreciated that these exemplary concentration percentages discussed herein can be a volume fraction (vol %) or a molar fraction (mol %). The second stage permeate gas flow 15p can be output from the second stage 15 so that it can be included in a recycle stream 19 that is recycled back toward the compressor system 11 to be combined with the biogas feed flow 2o and passed back through the membrane system 3 to enhance recovery of the methane output from the second stage 15. The second stage permeate gas flow 15p can be recovered at a pressure higher than atmospheric pressure, near atmospheric pressure, or at less than atmospheric pressure and may pass through a vacuum pump or compressor.

The second stage nonpermeate gas flow 15o output from the second stage 15 can be comprised mostly of methane and can also include some $CO_2$ and $O_2$ therein. For example, the second stage nonpermeate gas flow 15o can include methane at a second stage methane nonpermeate gas flow concentration of between 90%-99.8% $CH_4$, 95%-99.5% $CH_4$, 95%-99.8% $CH_4$, or 97%-99.8% $CH_4$. As other examples, the second stage nonpermeate gas flow 15o can include methane at a second stage methane nonpermeate gas flow concentration of greater than 94% $CH_4$, greater than 95% $CH_4$, greater than 98% $CH_4$, greater than 99% $CH_4$, or greater than 99.5% $CH_4$. The second stage nonpermeate gas flow 15o can include a second stage $O_2$ nonpermeate gas flow concentration that is up to 1% $O_2$ (e.g. between 0% and 1.0% $O_2$) or that is within a range of less than or equal to 0.2% $O_2$, 0.1-0.2% $O_2$, 0.05%-0.20% $O_2$, or less than 1% $O_2$. The second stage nonpermeate gas flow 15o can also include a second stage $CO_2$ nonpermeate gas flow concentration as the remaining portion of the nonpermeate gas flow 15o. For instance, second stage nonpermeate gas flow 15o can also include a second stage $CO_2$ nonpermeate gas flow concentration that is within the range of up to 10% $CO_2$, up to 5% $CO_2$, up to 2% $CO_2$, less than 2% $CO_2$, less than 1% $CO_2$, up to 0.5% $CO_2$, less than 0.5% $CO_2$, less than 0.1% $CO_2$, or up to 0.1% $CO_2$. As mentioned previously, it should be appreciated that these exemplary concentration percentages discussed herein can be a volume fraction (vol %) or a molar fraction (mol %). The nonpermeate gas flow 15o stream output from the second stage 15 can be nearly the same as the feed pressure of the feed flow fed to the second stage 15 (e.g. the pressure of the first stage nonpermeate flow 13np fed to the second stage 15).

The second stage nonpermeate gas flow 15o can be a membrane system output flow 3o that provides a product gas that is comprised mostly of methane and is suitable for being injected to a methane gas pipeline 4 (e.g. a natural gas pipeline). The second stage nonpermeate gas flow 15o can be a membrane system output flow 3o that is also, or alternatively for being output to a CHP and/or methane storage vessel for subsequent transport, sale, and/or use.

The third stage 17 of the membrane system 3 can receive the permeate gas flow 13p output from the first stage 13 via a first stage permeate flow feed conduit positioned between the first stage 13 and the third stage 17. The feeding of the first stage permeate flow 13p to the third stage 17 can be provided so that the first stage permeate flow does not undergo any compression or other increase in pressure before being fed to the third stage 17. The third stage permeate pressure can be maintained at a feed to permeate pressure ratio within the range of 1.5 to 15, 1.5 to 10, 2 to 10, or 3 to 7. As mentioned above, the permeate pressure ratio can be the pressure ratio of feed pressure ($P_f$)/permeate pressure ($P_p$) $P_f/P_p$, where $P_f$ and $P_p$ are the feed and permeate pressures on either side of the membrane in absolute pressure rather than gauge pressure (e.g. ratio of $P_f/P_p$ for the third stage 17 can be [pressure of the first stage permeate flow 13p]/[pressure of the third stage permeate gas flow 17o]).

The third stage 17 can include at least one membrane (e.g. the third stage 17 can include a single membrane or can utilize a plurality of membranes that are arranged in series or are arranged in parallel). The at least one membrane of the third stage 17 can be configured so that the first stage permeate flow 13p is passed into the third stage 17 and contacts the membrane structure within the vessel of the third stage 17. The membrane(s) can be composed so that the $CO_2$ component of the first stage permeate flow 13p passes quickly through the membrane structure to be output as a third stage permeate gas flow 17o, or fast gas flow, while the methane component of the first stage permeate flow 13p fed to the third stage 17 passes through the membrane structure at a substantially slower speed so that a substantial portion of the $CO_2$ can be separated from the methane within the gas fed to the third stage 17 and the majority of the methane within the first stage permeate flow 13p fed to the third stage 17 can be output as a third stage nonpermeate flow 17np for recycling back to the compressor system 11 by being incorporated into recycle stream 19 for being fed to the compressor system 11 via a recycle conduit 19a. The recycle stream 19 can be mixed with the biogas feed flow 2o before undergoing compression or can be fed separately to the compressor system 11 via a compressor recycling feed conduit 19b of the recycle stream conduit 19a as indicated by broken line in FIG. 2.

In some embodiments, the second stage permeate gas flow 15p can be mixed with the third stage nonpermeate flow 17np for forming a recycle stream 19 that is recycled to the compressor system 11 via recycle conduit 19a. In other embodiments, these flows can be separately recycled back to the compressor system 11 (e.g. recycled directly to the compressor system 11 or recycled to a position upstream of the compressor system for feeding to the compressor system 11) via separate recycle stream conduits.

The membrane of the third stage 17 can be composed so that the $O_2$ within the first stage permeate flow 13p fed to the third stage 15 passes through the membrane structure as well (e.g. is within the "fast gas" flow, or the third stage permeate gas flow 17o that also includes a substantial part of the $CO_2$ within the first stage permeate flow 13p).

The third stage permeate gas flow 17o output from the third stage 17 can be comprised mostly of $CO_2$ and can also include some methane and $O_2$ therein. For example, the third stage permeate gas flow 17o can include $CO_2$ at a third stage $CO_2$ permeate gas flow concentration of between 85%-99.9% $CO_2$, 85%-99.5% $CO_2$, 90%-99.9% $CO_2$, 95%-99.5% $CO_2$, or 95%-99.9% $CO_2$. The third stage permeate gas flow 17o can include a third stage $O_2$ permeate gas flow concentration within a range of less than or equal to 5% $O_2$, less than or equal to 4% $O_2$, less than or equal to 2% $O_2$, 0.1%-0.4% $O_2$, or 0.1%-1.0% $O_2$. The third stage permeate gas flow 17o can also include a third stage methane permeate gas flow concentration as the remaining portion of the permeate gas flow fed into the third stage 17. For instance, third stage permeate gas flow 17o can also include a third stage methane permeate gas flow concentration that is within the range of less than or equal to 15% $CH_4$, less than or equal to 6% $CH_4$, less than or equal to 5% $CH_4$, or less than or equal to 1.0% $CH_4$. As mentioned previously, it should be appreciated that these exemplary concentration percentages discussed herein can be a volume fraction (vol %) or a molar fraction (mol %). The third stage permeate gas flow 17o can be recovered at a pressure higher than atmospheric pressure, near atmospheric pressure, or at less than atmospheric pressure and may pass through a vacuum pump or compressor.

The third stage permeate gas flow 17o can be output from the third stage 17 so that it can be vented to the environment (e.g. output as exhaust). In other embodiments, the third stage permeate gas flow 17o can be fed to a carbon capture system or output for providing a source of $CO_2$ gas or a process stream for another use of a plant (e.g. use as a flue gas, use as a process stream for use in one or more heat exchangers before being output from the plant or stored in a vessel, etc.).

The third stage nonpermeate gas flow 17np output from the third stage 17 can be comprised mostly of methane and can also include some $CO_2$ and $O_2$ therein. For example, the third stage nonpermeate gas flow 17np can include methane at a third stage methane nonpermeate gas flow concentration of between 25%-95% $CH_4$, 30%-90% $CH_4$, 30%-80% $CH_4$, or 30%-50% $CH_4$. The third stage nonpermeate gas flow 17np can include a third stage $O_2$ nonpermeate gas flow concentration within a range of 0.2%-7% $O_2$, 0.5%-5% $O_2$, 0.5%-4% $O_2$, 0.7%-3% $O_2$, up to 7% $O_2$, up to 5% $O_2$, less than or equal to 2% $O_2$, 0.2%-2.0% $O_2$, 0.4%-1.0% $O_2$, 0.5-0.9% $O_2$, or 0.4%-0.9% $O_2$. The third stage nonpermeate gas flow 17np can also include a third stage $CO_2$ nonpermeate gas flow concentration as the remaining portion of the nonpermeate gas flow 17np. For instance, third stage nonpermeate gas flow 17np can also include a third stage $CO_2$ nonpermeate gas flow concentration that is within the range of 5%-75% $CO_2$, 5%-70% $CO_2$, 10%-70% $CO_2$, 20%-70% $CO_2$, 50%-70% $CO_2$, 5%-50% $CO_2$, or 5%-15% $CO_2$. As mentioned previously, it should be appreciated that these exemplary concentration percentages discussed herein can be a volume fraction (vol %) or a molar fraction (mol %). The third stage nonpermeate gas flow 17np stream output from the third stage can have a pressure that can be nearly the same as the pressure of the feed fed to the third stage 17 (e.g. the pressure of the first stage permeate gas flow 13p fed to the third stage).

In embodiments in which nitrogen is present in a small amount of the feed, the methane concentrations of different permeate gas flows and nonpermeate gas flows of the different stages of the membrane system (e.g. first stage 13, second stage 15, and/or third stage 17) can be determined in such a way that it also includes the nitrogen concentration within the determined methane concentration of the flow, which can inflate the methane concentration value (e.g. when nitrogen is present in a small amount within the feed, the methane concentration in different membrane output flows can be inflated by up to 10% in embodiments where the nitrogen and methane concentrations are grouped together as being a methane concentration due to the presence of nitrogen). This approach can be utilized in some embodiments because the nitrogen is present in a relatively small amount and, due to its properties, acts similarly to the methane when contacting a membrane structure, (e.g., nitrogen and methane both do not pass easily through a membrane structure). When this approach is utilized, the presence of the nitrogen can slightly affect some methane concentrations so that they will be inflated because the nitrogen concentration is included within the determined methane concentration. In other embodiments, the methane concentrations can be determined without grouping any nitrogen within the gas flows as being within the methane such that this slight inflation of the methane concentration is not present. While the presence of nitrogen may inflate some methane concentration values slightly for some embodiments, this has no effect on any calculation of methane recovery from utilization of embodiments of the membrane system 3.

Embodiments of the membrane system 3 can be configured to recover 99.5%-90% of the methane fed to the membrane system 3 via the biogas system 2. The oxygen reduction factor resulting from the embodiments of the membrane system 3 can be more than 5.0, more than 1.0, more than 0.75, be between 0.9-1.5, or be between 0.9 and 2.2. The oxygen rejection factor can be defined as the ratio of the molar concentration of oxygen within the biogas feed flow 2o to the molar concentration of the oxygen within the second stage nonpermeate gas flow 15o, which can be the upgraded biogas output flow 3o (e.g. [molar concentration of oxygen within the biogas feed flow 2o]/[molar concentration of the oxygen within the second stage nonpermeate gas flow 15o]).

The membranes of the first, second, and third stages 13, 15, and 17 of the membrane system 3 can each be configured to have a relatively low pre-selected selectivity for $CO_2$ over $O_2$ (also referred to as a $CO_2/O_2$ selectivity). This relatively low pre-selected $CO_2/O_2$ selectivity can be achieved by choosing a membrane material having said selectivity properties. For example, the chosen membrane may have the pre-selected selectivity for $CO_2$ over $O_2$ at a temperature of 30° C. that is less than 5, less than 4.5, between 3.0 and 5.0, or between 3.4 and 4.5. The relatively low pre-selected $CO_2/O_2$ selectivity may also be achieved by choosing a membrane material with a selectivity greater than 4.5 at 30° C., but operating the membrane system at an elevated temperature that is over 30° C. where the membrane selectivity would fall below 4.5 at the elevated temperature (e.g. be between 3.4 and 4.5, be less than or equal to 3.5, etc.). The relatively low pre-selected $CO_2/O_2$ selectivity may also be achieved by choosing a membrane material with a selectivity less than 3.0 at 30° C., but operating the membrane system at a lower temperature below 30° C. where the membrane selectivity would increase to a number that is between 3.0 and 5.0 or between 3.4 and 4.5 at the lower temperature.

The membranes of the first, second and third stages 13, 15, and 17 can also utilize relatively low carbon dioxide over methane selectivity values (also referred to as $CO_2/CH_4$ selectivity values). For example, embodiments can utilize $CO_2/CH_4$ selectivity values of between 25 and 45, between 30 and 40, or less than 45 and above 16. The $CO_2/CH_4$ selectivity values of the membranes can be values that correspond with the $CO_2/O_2$ selectivity values that are less than 5, less than 4.5, between 3.0 and 5.0, or between 3.4 and 4.5, for example.

Some embodiments can be utilized such that all the membranes of the first, second, and/or third stages of the membrane system 3 utilize such $CO_2/O_2$ selectivity values and $CO_2/CH_4$ selectivity values. Other embodiments can be designed and utilized so that the first stage 13 and the third stage 17 utilize membranes having such $CO_2/O_2$ selectivity values and $CO_2/CH_4$ selectivity values while the second stage 15 may utilize membranes having different selectivity values (e.g. much higher $CO_2/O_2$ selectivity values, etc.). Yet other embodiments can be configured so that only each and every membrane of only the second stage 15, only the third stage 17, or only the first stage 13 have such $CO_2/O_2$ selectivity values. Yet other embodiments can be provided so that only some of the membranes of some of these stages utilize such $CO_2/O_2$ selectivity values. The use of a low selectivity of $CO_2$ over $O_2$ was surprisingly found to provide improved production results since, conventionally, it has been desired to utilize high selectivity of $CO_2$ over $O_2$ to obtain sufficiently high concentrations of methane in an output product gas.

Traditionally, removal of low or trace quantities of a gas, such as oxygen in this case, has been accomplished by using high permeability membranes which permeate $CO_2$ and $O_2$ at very high rates but have a reduced selectivity for slower gases such as methane and nitrogen. This conventional approach is typically done to target the highest $CO_2/CH_4$ selectivity, which leads to use of a very high $CO_2/O_2$ selectivity as the $CO_2/CH_4$ selectivity and $CO_2/O_2$ selectivity cannot be independently manipulated.

In contrast to this conventional approach, the membranes that can be utilized in embodiments of the biogas upgrading systems, membrane arrangements, and apparatuses utilizable in such systems as described herein, and methods of making and using the same, surprisingly and unexpectedly balance high enough $CO_2/CH_4$ selectivity so that biomethane can be enriched and recycle flows are not too high, but low enough that the $CO_2/O_2$ selectivity is not so high such that the multiple stage process can reject the $O_2$ along with the $CO_2$ sufficiently to allow for a relatively low oxygen concentration in the enriched methane output from the multiple stage membrane system 3 while also providing high methane recovery.

Membranes that can be utilized in the first, second, and third stages 13, 15, and 17, may be manufactured as hollow fibers and packaged as membrane bundles or wound membrane cartridges, or be flat sheets, packaged as spiral wound or plate and frame units. For example, some preferred embodiments can utilize hollow fiber membrane units containing hollow fiber membranes made from polymers. Examples of polymers used to make membranes that provide a pre-selected $CO_2/O_2$ selectivity for a pre-selected operational temperature include, but are not limited to, polystyrene, polysulfone, polyethersulfone, polyvinyl fluoride, polyvinylidene fluoride, polyether ether ketone, polycarbonate, polyphenylene oxide, polyethylene, polypropylene, cellulose acetate, polyimide (such as Matrimid 5218 or P-84), polyamide, polyvinyl alcohol, polyvinyl acetate, polyethylene oxide, polydimethylsiloxane, copolymers, block copolymers, or polymer blends. The hollow fiber membranes may be asymmetric with a nonporous layer or may contain a porous support with a nonporous coating. The coating may be applied to the inner or outer surface of the hollow fiber.

In some embodiments of the membrane stages, a plurality of hollow fiber membranes can create a membrane bundle, which can be held together at one or both ends by a tubesheet made of thermoplastic or thermoset materials. Examples of tubesheet materials include cured epoxy or polyurethane-based formulations. In some embodiments, the hollow fiber membrane bundle can be housed in a vessel, which may range in diameter from 25.4 mm to 254 mm (1 to 10 inches) and vary in length from 305 mm to 3050 mm (1 to 10 feet). The vessel may be constructed of plastic, metal, or other suitable materials. The vessel can have at least one fluid port in fluid flow communication with the shell side of the hollow fiber membranes. The vessel can also have at least one port in fluid flow communication with the bore side of the hollow fiber membranes and may have another port in fluid flow communication with the opposite end of the hollow fiber membrane. The tubesheet can serve to separate the bore side fluids from the shell side fluids. The feed gas may be introduced to the bore side or the shell side of the membrane.

Figure 3:
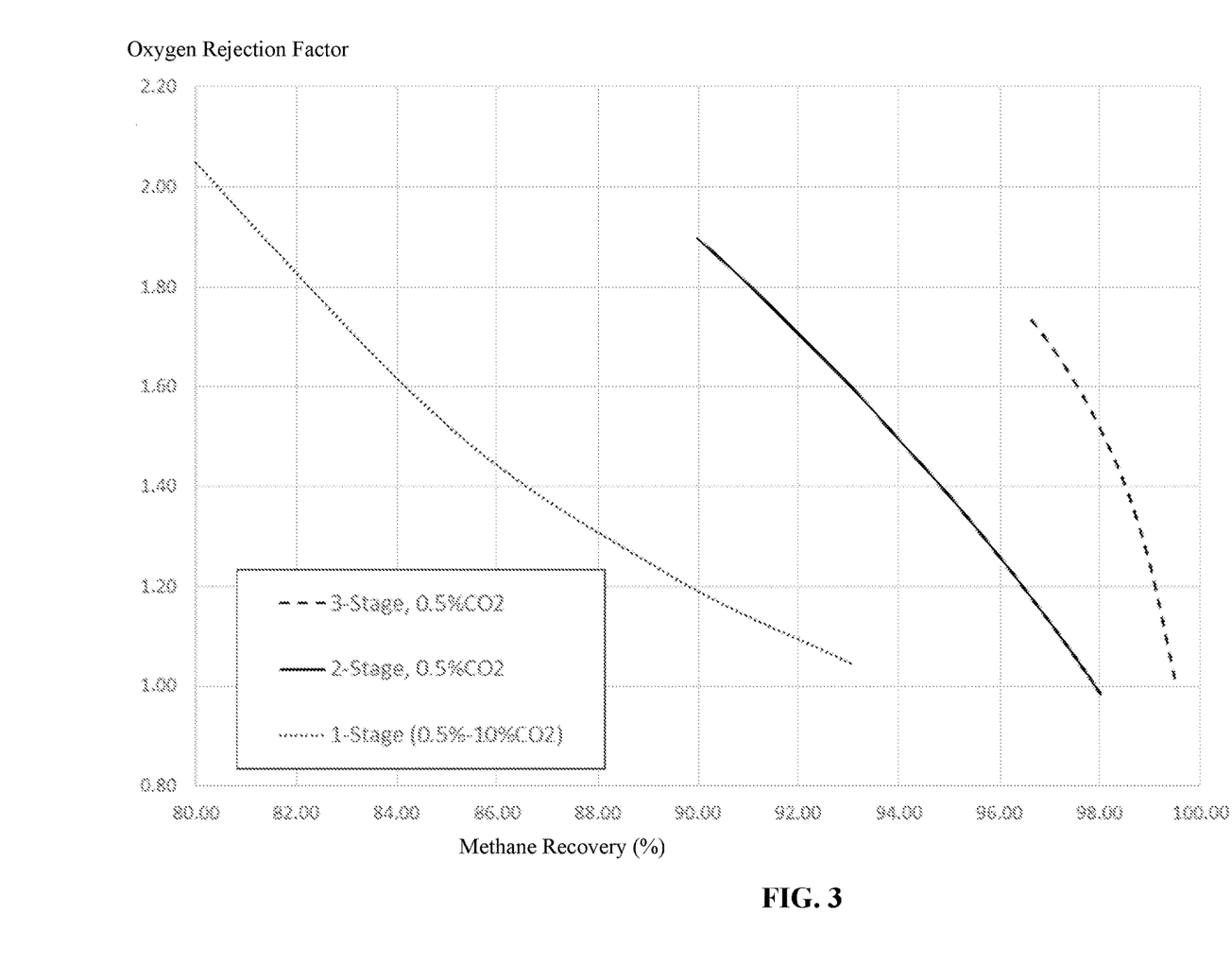
FIG. 3 is a graph illustrating a level of methane recovery (x-axis, in percent, %) in relation to the oxygen rejection factor (e.g. mol % $O_2$ in feed/mol % $O_2$ in the biogas output) utilizing systems that have a single stage membrane arrangement, a two stage membrane arrangement and a three stage membrane arrangement.

FIG. 3 illustrates simulation results of how embodiments of the membrane system 3 utilizing one stage, two stage, and three stage embodiments of the membrane system having membranes using a low selectivity of $CO_2$ over $O_2$ would be expected to perform when operated at a pressure of 14 barg and a temperature of 20° C. at a flow rate of 1000 nmch (normal cubic meters per hour) at a biogas feed composition of 59.88 mol % $CH_4$, 39.93 mol % $CO_2$ and 0.2% $O_2$. As shown in FIG. 3, for one and two stage membrane systems, there is a significant trade-off between achieving high recovery and high oxygen reduction, where often the best results for methane recovery would be expected to be obtained when the $O_2$ reduction factor was below about 1.2.

However, it was surprisingly found that oxygen reduction can be improved with only a modest sacrifice in recovery when using a membrane material having a decreased $CO_2/O_2$ selectivity. The lower selectivity value results in more oxygen permeating each stage of the membrane system 3 with the $CO_2$, which helps facilitate removal of the oxygen from the methane of the upgraded biogas output flow 3o.

The below Table 1 illustrates an example of how embodiments of the membrane system 3 having a configuration similar to the configuration of the exemplary embodiment shown in FIG. 2 would perform using membranes in the first, second, and third stages 13, 15, and 17 at different $CO_2/O_2$ selectivity values ranging from 5 to 3.4 at a reference temperature of 30° C. The below Table 1 provides simulation results for an embodiment of the membrane system 3 that operates to obtain a second nonpermeate stream 15o containing 0.5 mol % $CO_2$ with 99.5% recovery of methane and is operational at 14 barg and 20° C. using membranes comprised of polymeric hollow fibers with the listed variable $CO_2/O_2$ selectivity values:

TABLE 1

| $CO_2/O_2$ Selectivity @ 30° C. | mol % $O_2$ in second stage nonpermeate flow 15o | $O_2$ Rejection Factor |
| --- | --- | --- |
| 5 | 0.24 | 0.82 |
| 4.9 | 0.24 | 0.83 |
| 4.8 | 0.24 | 0.84 |
| 4.7 | 0.23 | 0.86 |
| 4.6 | 0.23 | 0.87 |
| 4.5 | 0.23 | 0.89 |
| 4.4 | 0.22 | 0.90 |
| 4.3 | 0.22 | 0.92 |
| 4.2 | 0.21 | 0.94 |
| 4.1 | 0.21 | 0.97 |
| 4.0 | 0.20 | 0.99 |
| 3.9 | 0.20 | 1.01 |
| 3.8 | 0.19 | 1.05 |
| 3.7 | 0.18 | 1.09 |
| 3.6 | 0.18 | 1.13 |
| 3.5 | 0.17 | 1.17 |
| 3.4 | 0.16 | 1.22 |

As can be appreciated from the above, the use of membranes with a low selectivity value was found to provide an oxygen concentration in the second stage nonpermeate gas flow 15o, which can be the upgraded biogas output flow 3o, to be at or below 0.2 mol %. In the above examples, use of such a selectivity of less than or equal to 4.0 or less than or equal to 3.5 could provide such reduced oxygen levels. Such a result can permit the output flow 3o to meet highly stringent methane pipeline oxygen specifications that can require oxygen to be at or below 0.2 mol % to help avoid dangerous conditions (e.g. accelerated corrosion of pipeline conduit material).

Figure 4:
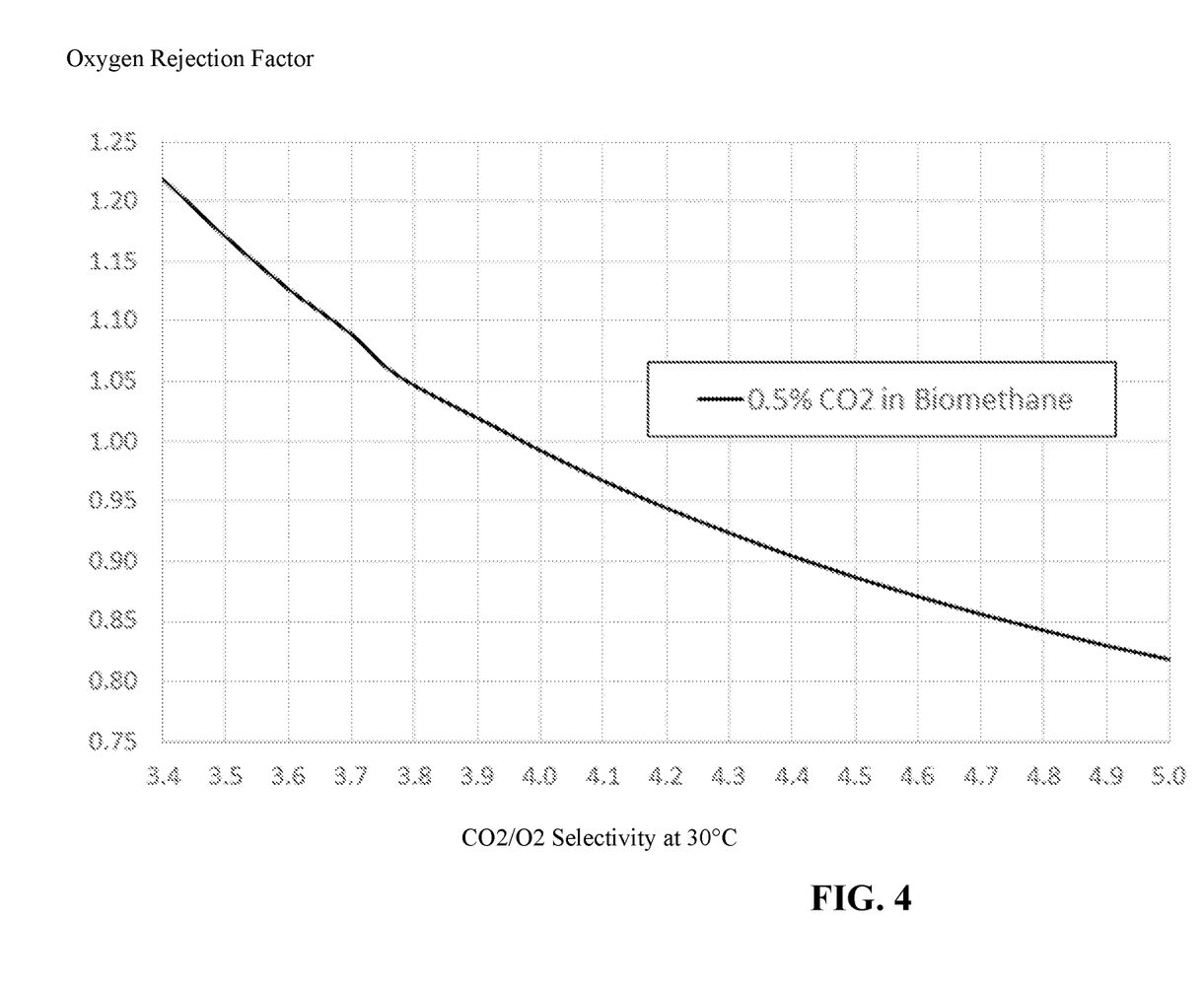
FIG. 4 is a graph illustrating the relationship between the oxygen rejection factor (mol % $O_2$ in feed/mol % $O_2$ in the biogas output) and $CO_2/O_2$ selectivity when utilizing embodiments of the exemplary biogas upgrading system 1 for an upgraded biogas output flow 3o having methane within a first prescribed methane concentration, $CO_2$ within a first prescribed $CO_2$ concentration of less than or equal to 0.5%, and $O_2$ within a first prescribed $O_2$ concentration of less than or equal to 0.2%

FIG. 4 also illustrates results of the above simulation. FIG. 4 illustrates how the $CO_2/O_2$ selectivity value of the membranes for the first, second, and third stages 13, 15, and 17 affected the oxygen rejection factor for obtaining the second stage nonpermeate gas flows 15o listed in Table 1. It was surprisingly found that use of a lower $CO_2/O_2$ selectivity value for the membranes provided a higher oxygen rejection factor while still producing a high methane purity product suitable for meeting highly stringent pipeline oxygen content specifications and providing high recovery. As can be appreciated from FIG. 4, oxygen rejection factors as high as 1.2-1.0 could be generated in embodiments of the membrane system while still providing a highly purified methane content for the upgraded biogas output flow 3o and providing a 99.5% recovery of the methane (e.g. 99.5% of the methane within the feed fed to the membrane system 3 was recovered within the product flow output from the system).

This is a surprising and unexpected result. Conventionally, it was believed that low levels of oxygen within an output flow could not be obtained using membranes without substantially lowering methane recovery. (See e.g. paragraph 9 of U.S. Pat. App. Pub. 2011/0094378). In contrast to this conventional viewpoint, embodiments of the biogas upgrading system 1 and/or membrane system 3 can provide high levels of methane recovery (e.g. a recovery of 99.5%) while also providing very low oxygen concentrations within the upgraded biogas output flow 3o.

Embodiments of the biogas upgrading system 1 and/or membrane system 3 can be configured to provide process flexibility. If the oxygen is found to concentrate in the upgraded biogas output flow 3o to an undesired level or otherwise deplete the methane within the biogas output flow 3o, the membrane system 3 can be operated to provide improved rejection of oxygen within the membrane stages of the membrane system 3 to remove more oxygen to address this situation. For example, more oxygen can be output as the third stage permeate flow 17o. Such operational flexibility can be enhanced by utilization of membranes within the stages of the membrane system that have a low $CO_2/O_2$ selectivity value as discussed herein. Moreover, embodiments can be provided that can provide the upgraded biogas output flow 3o without requiring use of a PSA system and/or a catalytic system to further remove oxygen from the upgraded biogas output flow 3o before that flow is fed to the pipeline 4.

It should be appreciated that modifications to the embodiments explicitly shown and discussed herein can be made to meet a particular set of design objectives or a particular set of design criteria. For instance, the arrangement of valves, piping, and other conduit elements (e.g. conduit connection mechanisms, tubing, seals, etc.) for interconnecting different units of the biogas upgrading system and/or membrane system for fluid communication of the flows of fluid between different units can be arranged to meet a particular plant layout design that accounts for available area of the plant, sized equipment of the plant, and other design considerations. As another example, the flow rate, pressure, and temperature of the fluid passed through the different stages of the membrane system as well as passed through other system elements can vary to account for different plant design configurations and other design criteria. As yet another example, the number of membrane stages and how they are arranged can be adjusted to meet a particular set of design criteria. As yet another example, the material composition for the different structural components of the membranes, compressor system, and biogas system can be any type of suitable materials as may be needed to meet a particular set of design criteria.

It should be appreciated that embodiments of the biogas upgrading system 1, or membrane system 3 can be configured as a standalone plant or be incorporated into another type of plant (e.g., a biogas plant having at least one biogas system 2) in which at least one membrane system 3 can be utilized. The plant biogas upgrading system 1 and membrane system 3 can each be configured to include process control elements positioned and configured to monitor and control operations (e.g. temperature and pressure sensors, flow sensors, an automated process control system having at least one work station that includes a processor, non-transitory memory and at least one transceiver for communications with the sensor elements, valves, and controllers for providing a user interface for an automated process control system that may be run at the work station and/or another computer device of the plant, etc.).

As another example, it is contemplated that a particular feature described, either individually or as part of an embodiment, can be combined with other individually described features, or parts of other embodiments. The elements and acts of the various embodiments described herein can therefore be combined to provide further embodiments. Thus, while certain exemplary embodiments of biogas upgrading systems, membrane arrangements and apparatuses utilizable in such systems, and methods of making and using the same have been shown and described above, it is to be distinctly understood that the invention is not limited thereto but may be otherwise variously embodied and practiced within the scope of the following claims.

What is claimed is:

1. A process for purifying a biogas feed flow via removal of oxygen ($O_2$) and carbon dioxide ($CO_2$), the process comprising:

providing the biogas feed flow to a first stage of a membrane system to produce a first stage nonpermeate flow and a first stage permeate flow, the biogas feed flow comprising between 30 mol % and 80 mol % methane, between 20 mol % and 70 mol % $CO_2$, and between 0.2 mol % and 3 mol % $O_2$, the first stage nonpermeate flow being comprised of methane, $O_2$, and $CO_2$ such that the first stage nonpermeate flow has a lower concentration of $CO_2$ than the first stage permeate flow, the first stage permeate flow being comprised of methane, $O_2$, and $CO_2$ and having a lower methane concentration than the first stage nonpermeate flow; and supplying the first stage nonpermeate flow to a second stage of the membrane system to produce a second stage nonpermeate flow and a second stage permeate flow, the second stage nonpermeate flow comprising at least 90 mol % methane and less than 1 mol % $O_2$, the second stage permeate flow having a $CO_2$ content that is greater than a $CO_2$ content of the second stage nonpermeate flow;

wherein the oxygen reduction factor of the process is the ratio of the molar concentration of $O_2$ within the biogas feed flow and the molar concentration of $O_2$ within the second stage nonpermeate flow; and
wherein the process is performed so that the oxygen reduction factor is between 0.9 and 2.2.

2. The process of claim 1, comprising:
supplying the first stage permeate flow to a third stage of the membrane system to produce a third stage nonpermeate flow and a third stage permeate flow; and
providing the third stage nonpermeate flow to form a recycling stream for feeding the third stage nonpermeate flow to the first stage or a compressor system.

3. The process of claim 2, wherein the recycling comprises:
mixing the third stage nonpermeate flow with the second stage permeate flow to form the recycling stream before feeding the recycling stream to the compressor system for undergoing compression to a pre-selected pressure.

4. The process of claim 3, comprising:
mixing the recycling stream with the biogas feed flow before the biogas feed flow is fed to the compressor system, the compressor system being upstream of the membrane system.

5. The process of claim 1, comprising:
supplying the first stage permeate flow to a third stage of the membrane system to produce a third stage nonpermeate flow and a third stage permeate flow;
wherein at least one membrane of the first stage has a $CO_2/O_2$ selectivity value between 3.4 and 4.5 when at a temperature of 30° C.; and
wherein at least one membrane of the third stage has a $CO_2/O_2$ selectivity value of between 3.4 and 4.5 when at a temperature of 30° C.

6. The process of claim 1, wherein at least one membrane of the first stage has a $CO_2/O_2$ selectivity value of between 3.4 and 4.5 when at a temperature of 30° C.

7. The process of claim 1, wherein each and every membrane of the first stage, each and every membrane of the second stage, and/or each and every membrane of the third stage has a $CO_2/O_2$ selectivity value of between 3.4 and 4.5 when at a temperature of 30° C.

8. The process of claim 1, wherein the process is performed so that the oxygen reduction factor is between 1.0 and 1.25.

9. The process of claim 1, wherein the second stage nonpermeate flow is an upgraded biogas output flow having a methane content of at least 95 mol % methane.

10. The process of claim 1, wherein the second stage nonpermeate flow has less than or equal to 0.2 mol % $O_2$.

11. A biogas upgrading system, comprising:
a membrane system configured to receive a biogas feed flow output from a biogas system, the biogas feed flow comprising between 30 mol % and 80 mol % methane, between 20 mol % and 70 mol % $CO_2$, and between 0.2 mol % and 3 mol % $O_2$, the membrane system comprising:
a first stage positioned and configured to receive the biogas feed flow to produce a first stage nonpermeate flow and a first stage permeate flow, the first stage nonpermeate flow being comprised of methane, $O_2$, and $CO_2$ such that the first stage nonpermeate flow has a lower concentration of $CO_2$ than the first stage permeate flow, the first stage permeate flow being comprised of methane, $O_2$, and $CO_2$ and having a lower methane concentration than the first stage nonpermeate flow; and a second stage connected to the first stage to receive the first stage nonpermeate flow to produce a second stage nonpermeate flow and a second stage permeate flow, the second stage nonpermeate flow comprising at least 90 mol % methane and less than 1 mol % $O_2$, the second stage permeate flow having a $CO_2$ content that is greater than a $CO_2$ content of the second stage nonpermeate flow;
wherein the oxygen reduction factor of the biogas upgrading system is the ratio of the molar concentration of $O_2$ within the biogas feed flow and the molar concentration of $O_2$ within the second stage nonpermeate flow; and
wherein the biogas upgrading system is configured so that the oxygen reduction factor is between 0.9 and 2.2.

12. The biogas upgrading system of claim 11, comprising:
a third stage connected to the first stage to receive the first stage permeate flow and produce a third stage nonpermeate flow and a third stage permeate flow, the third stage connected to a recycle conduit such that the third stage nonpermeate flow is passable through the recycle conduit to a position upstream of the first stage of the membrane system.

13. The biogas upgrading system of claim 12, comprising:
a compressor system positioned upstream of the first stage to compress the biogas feed flow before the biogas feed flow is fed to the first stage, the third stage connected to the recycle conduit such that the third stage nonpermeate flow is passable through the recycle conduit to the compressor system without use of another compressor system.

14. The biogas upgrading system of claim 13, wherein the recycle conduit is configured to mix the third stage nonpermeate flow with the second stage permeate flow to form a recycling stream before feeding the recycling stream to the compressor system for undergoing compression to a pre-selected pressure.

15. The biogas upgrading system of claim 11, and the second stage nonpermeate flow has less than or equal to 0.2 mol % $O_2$.

16. The biogas upgrading system of claim 11, wherein at least one membrane of the first stage has a $CO_2/O_2$ selectivity value of between 3.4 and 4.5 when at a temperature of 30° C.

17. The biogas upgrading system of claim 11, wherein:
at least one membrane of the first stage, at least one membrane of the second stage, and/or at least one membrane of the third stage has a $CO_2/O_2$ selectivity value of between 3.4 and 4.5 when at a temperature of 30° C.; or
each and every membrane of the first stage, each and every membrane of the second stage, and/or each and every membrane of the third stage has a $CO_2/O_2$ selectivity value of between 3.4 and 4.5 when at a temperature of 30° C.

18. The biogas upgrading system of claim 11, wherein the biogas upgrading system is configured so that the oxygen reduction factor is between 1.0 and 1.25.

19. The biogas upgrading system of claim 11, wherein the second stage nonpermeate flow is an upgraded biogas output flow having a methane content of at least 95 mol % methane.

20. The biogas upgrading system of claim 11, comprising:
the biogas system, the biogas system comprising at least one digester that forms the biogas feed flow and at least one biogas cleaning device positioned to treat the biogas feed flow before the biogas feed flow is fed to the first stage of the membrane system.

* * * * *